(12) United States Patent
Bar-Or et al.

(10) Patent No.: US 7,070,937 B1
(45) Date of Patent: Jul. 4, 2006

(54) MARKER USEFUL FOR DETECTION AND MEASUREMENT OF FREE RADICAL DAMAGE AND METHOD

(75) Inventors: David Bar-Or, Englewood, CO (US); Edward Lau, Boulder, CO (US)

(73) Assignee: Ischemia Technologies, Inc., Waltham, MA (US)

( * ) Notice: Subject to any disclaimer, the term of this patent is extended or adjusted under 35 U.S.C. 154(b) by 0 days.

(21) Appl. No.: 09/820,416

(22) Filed: Mar. 29, 2001

Related U.S. Application Data

(63) Continuation of application No. PCT/US99/22746, filed on Oct. 1, 1999, which is a continuation-in-part of application No. 09/165,961, filed on Oct. 2, 1998, now Pat. No. 6,475,743.

(60) Provisional application No. 60/102,962, filed on Oct. 2, 1998.

(51) Int. Cl.
*G01N 33/53* (2006.01)
*G01N 33/537* (2006.01)
*G01N 33/543* (2006.01)
*C12Q 1/50* (2006.01)

(52) U.S. Cl. .................. 435/7.1; 435/17; 435/7.92

(58) Field of Classification Search .................. 435/7.1, 435/7.92, 17
See application file for complete search history.

(56) References Cited

U.S. PATENT DOCUMENTS

| | | | |
|---|---|---|---|
| 3,955,926 A | 5/1976 | Fischer | 23/230 |
| 4,230,601 A | 10/1980 | Hill | 252/408 |
| 4,337,064 A | 6/1982 | Gindler | 23/230 |
| 4,379,848 A | 4/1983 | Yeaw | 436/84 |
| 4,434,234 A | 2/1984 | Adams et al. | 436/86 |
| 4,468,466 A | 8/1984 | Morrissey | 436/86 |
| 4,486,282 A | 12/1984 | Bier | 204/180 |
| 4,492,753 A | 1/1985 | Shell et al. | |
| 4,510,383 A | 4/1985 | Ruppender | 235/462 |
| 4,568,647 A | 2/1986 | Sanford | 436/88 |
| 4,569,794 A | 2/1986 | Smith et al. | 260/113 |
| 4,592,893 A | 6/1986 | Poppe et al. | 422/56 |
| 4,713,327 A | 12/1987 | Findlay et al. | 435/17 |
| 4,786,605 A | 11/1988 | Mauck et al. | 436/86 |
| 4,960,710 A | 10/1990 | Lau | 436/86 |
| 5,077,222 A | 12/1991 | Lau | 436/88 |
| 5,141,855 A | 8/1992 | Schmittou | 435/34 |
| 5,169,936 A | 12/1992 | Staples et al. | 530/350 |

(Continued)

FOREIGN PATENT DOCUMENTS

| | | |
|---|---|---|
| WO | WO 00/20454 | 4/2000 |
| WO | WO 00/20840 | 4/2000 |
| WO | WO 00/52476 | 9/2000 |
| WO | WO 04/030522 | 4/2004 |

OTHER PUBLICATIONS

Ames et al., *Proc. Natl. Acad. Sci. USA*, 90:7915–7922 (1993).
Florence, *Australian and New Zealand J. Opthamol.*, 23(1):3–7 (1995).
Halliwell and Gutteridge, "Free Radicals in Biology and Medicine" pp. 1–21 (2nd ed. Clarendon Press—Oxford 1989).
Henderson's Dictionary of Biological Terms, 10th ed. Eleanor Lawrence, ed., John Wiley & Sons, NY, p. 252.
Kerr et al., Introduction to Oxygen Free Radicals, *Heart & Lung*, 25, 200–209 (1996).
Knight, Diseases Related to Oxygen–Derived Free Radicals, *Ann of Clin. Lab Sci.*, 25, 111–121 (1995).
Lakusta et al. (1979) *Journal of Inorganic Biochemistry* 11:303–315.
Malins et al., *Proc. Natl. Acad. Sci USA*, 93:2557–2565 (1996).
Manso, Ischemia, Reperfusion and Oxygen Free Radicals, *Rev. Port. Cardiol.*, 11, 997–999 (1992).
Mohanakrishnan et al. (1982) *Journal of Pharmaceutical Sciences*, 71(10):1180–1182.

(Continued)

*Primary Examiner*—Rodney P Swartz
*Assistant Examiner*—Khatol S Shahnan-Shah
(74) *Attorney, Agent, or Firm*—Swanson & Bratschun, LLC

(57) ABSTRACT

The present invention teaches a marker useful for detection and measurement of free radical damage. Specifically, the invention takes advantage of alterations which occur to the N-terminus of the albumin molecule, a circulating protein in human blood, in the presence of free radicals. These alterations effect the ability of the N-terminus of the albumin molecule to bind metals. Methods for detecting and quantifying this alteration include evaluating and quantifying the cobalt binding capacity of an albumin-containing sample, analysis and measurement of the ability of albumin to bind exogenous cobalt, detection and measurement of the presence of copper in a purified albumin sample and use of an immunological assay specific to the altered form of serum albumin which occurs following free radical damage. Also taught by the present invention is the use of the peptide Asp Ala His Lys and the compound Asp-Ala-His-Lys-R, wherein R is any chemical group capable of producing a detectable signal when a metal ion capable of binding to the N-terminus of naturally-occurring albumin is bound to the compound, for detection and quantitation of the marker. Methods of the present invention also include use of the marker as a "biochemical tag," thereby allowing for sensitive detection and measurement of the efficacy of clinical drugs and therapeutics which result in the generation of free radicals or which act to limit free radical damage. The marker also acts as a "biological tag" of a process implicated in a wide array of diseases and conditions and, accordingly, may be used to monitor and assess such diseases and conditions. Finally, the invention provides antibodies, immunoassays, and kits for use in detecting or quantitating the marker.

16 Claims, No Drawings

U.S. PATENT DOCUMENTS

| | | | | |
|---|---|---|---|---|
| 5,173,422 | A | 12/1992 | Knowles et al. | 435/240.27 |
| 5,173,431 | A | 12/1992 | Pugia et al. | 436/86 |
| 5,182,214 | A | 1/1993 | Kessler et al. | 436/88 |
| 5,223,392 | A | 6/1993 | Cohen | 435/7.1 |
| 5,225,354 | A | 7/1993 | Knowles et al. | 436/548 |
| 5,227,307 | A * | 7/1993 | Bar-Or et al. | 436/63 |
| 5,290,519 | A * | 3/1994 | Bar-Or et al. | 422/61 |
| 5,290,678 | A | 3/1994 | Jackowski | 435/7.4 |
| 5,326,707 | A | 7/1994 | Franke et al. | 436/86 |
| 5,503,987 | A | 4/1996 | Wagner et al. | 435/7.94 |
| 5,532,136 | A | 7/1996 | Carlson et al. | 435/7.92 |
| 5,569,608 | A | 10/1996 | Sommer | 436/518 |
| 5,604,105 | A | 2/1997 | Jackowski | |
| 5,620,856 | A | 4/1997 | Carlson et al. | 530/364 |
| 5,639,624 | A | 6/1997 | Wagner et al. | 435/7.92 |
| 5,654,160 | A | 8/1997 | Johnson | 435/7.1 |
| 5,656,729 | A | 8/1997 | Fuluhata et al. | 435/7.9 |
| 5,670,627 | A | 9/1997 | Johnson | 530/388.9 |
| 5,670,645 | A | 9/1997 | Johnson | 546/141 |
| 5,683,907 | A | 11/1997 | Johnson | 436/518 |
| 5,710,008 | A | 1/1998 | Jackowski | |
| 5,744,358 | A | 4/1998 | Jackowski | 435/7.4 |
| 5,747,274 | A | 5/1998 | Jackowski | 435/7.94 |
| 5,876,969 | A | 3/1999 | Fleer et al. | |
| 5,994,339 | A * | 11/1999 | Crapo et al. | 514/185 |
| 6,020,204 | A | 2/2000 | DerVartanian et al. | 436/74 |
| 6,083,758 | A | 7/2000 | Imperiali et al. | 436/73 |
| 6,087,184 | A | 7/2000 | Magginetti et al. | 436/514 |
| 6,171,870 | B1 | 1/2001 | Freitag | 436/518 |
| 6,235,489 | B1 | 5/2001 | Jackowski | |
| 6,268,223 | B1 | 7/2001 | Cornell-Bell et al. | 436/514 |
| 6,274,305 | B1 | 8/2001 | Sonnenschein et al. | |
| 6,335,205 | B1 | 1/2002 | Bausback | 436/526 |
| 6,375,930 | B1 * | 4/2002 | Young et al. | 424/9.362 |
| 6,410,341 | B1 | 6/2002 | Freitag et al. | 436/514 |
| 6,444,432 | B1 | 9/2002 | Kleinfeld | 435/7.8 |
| 6,767,708 | B1 | 7/2004 | Williams et al. | |
| 2003/0017506 | A1 | 1/2003 | Bar-Or et al. | |
| 2004/0175754 | A1 | 9/2004 | Bar-Or et al. | |
| 2004/0209379 | A1 | 10/2004 | Bar-Or et al. | |

OTHER PUBLICATIONS

Pratico D. et al., "Localization of distinct F2–isoprostanes in human atherosclerotic lesions," *J. Clin. Invest.* 100(8):2028–2034 (1997).
Smith et al., Cytochemical Demonstration of Oxidative Damage in Alzheimer Disease by Immunochemical Enhancement . . . *Journal of Histochem & Cytochem.*, 46:731–735 (1998).
Ueda et al., *J. Inorgan. Biochem.*, 55:123–130 (1994).
Bar–Or et al., 2002, *Free Rad. Biol & Med.*, 32(2):197–1991.
Bar–Or et al., 2001, *Am. Heart J.*, 141(6):986–991.
Bar–Or et al., 2001, *Eur. J. Biochem*, 268:42–47.
Bar–Or et al., 2000, *J. Emergency Med.*, 19(4):311–315.
Bar–Or et al., 1999, *Ann Emergency Med.*, 3:Oct. 4, 1999, Part 2, S56.
U.S. Appl. No. 09/165,581, filed Oct. 2, 1998.
U.S. Appl. No. 09/165,926, filed Oct. 2, 1998.
U.S. Appl. No. 09/165,961, filed Oct. 2, 1998.
Afans'ev, Superoxide Ion: Chemistry and Biological Implications, vol. 1, pp. 26, 51, 147, 168–196, 248–266 (CRC Press, Boca Raton, FL) (1989).
Afans'ev, Superoxide Ion: Chemistry and Biological Implications, vol. II, pp. 138 and 187 (CRC Press, Boca Raton, FL) (1989).
Alberts et al., *Mol. Biol. Cell*, (2nd ed., Garland Publishing Inc. 1989).
Anderson, "Effects of na+k=2cl Cotransport Inhibition on Myocardial NA and CA During Ischemia and Reperfusion," found at http://www.uth.tmc.ed/apstracts/1995/cell/September/319c.html, p. 1 (Sep. 1995), published in APStracts on Sep. 23, 1995.
Bautista et al., *Biosci. Biotechnol. Biochem.*, 62(3):419–423 (1998).
Boehringer Mannheim Catalog No. 15947.
Braughler, "Calicum and Lipid Peroxidation," from Central Nervous System Diseases Research Unit, p. 99 (1987), The Upjohn Company, Kalamazoo, Michigan.
Chan, *Eur. J. Biochem.*, 227:524–528 (1995).
Cobbe, *J. Mol. Cell. Card.*, 12:745–760 (1980).
Cotelle et al., *J. Inorganic Biochem.*, 46:7–15 (1992).
"DNA Damage Linked to Risk of Breast Cancer Spread," found at http://www.pslgroup.com/dg/6c2e.htm.
Das et al., *Meth. Enzymol.*, 233:601–610 (1994).
Davies, *J. Free Radicals Biol. & Med.*, 2:155–173 (1986).
Davies, "Oxygen Radicals Stimulate Intracellular Proteolysis and Lipid Peroxidation by Independent Mechanisms in Erythrocytes," from the Dept. of Physiology and Biophysics, Harvard Medical School, *J. Biol. Chem.*, vol. 262, No. 17, issue of Jun. 15, pp. 8220–8225, (1987), Boston Massachusetts.
Davies et al., *J. Biological Chem.*, 262(20):9895–9901 (1987).
Davies et al., *J. Biological Chem.*, 262(20):9902–9907 (1987).
Davies et al., *J. Biological Chem.*, 262(20):9908–9913 (1987).
Davies et al., *J. Biological Chem.*, 262(20):9914–9920 (1987).
Dolovich et al., *Br. J Ind Med*, 41:51–55 (1984).
Fleming and Nixon, *Analytical Biochem*, 154:691–701 (1986).
Genest et al., *J Am Coll Cardiol*, 16:1114–9 (1990).
Gobel et al., *Eur. Heart J.*, 19:1208–1213 (1998).
Gomez, "Ruling Out Ischemia Saves Time and Money," vol. 6(9) pp. 148, 150, found at http://www.medscape.com/CPG/ClinRE...c0609.25.gomez/c0609.25.gomez.html, pp. 1–2, Clinicians Reviews 6:148, Clinicians Publishing Group and Williams & Wilkins, (1996) or *J. Am. Coll. Cardiol.* 28:25–33.
Gutteridge et al., *Biochim Biophys Acta*, 759:38–41 (1983).
Halliwell et al., *Arch Biochem Biophys*, 246(2):501–514 (1986).
Halliwell, Oxygen Radicals and Tissue Injury, Proceedings of Brook Lodge Symposium, pp. 100–104 (Apr. 1987), Augusta, Michigan.
Halliwell et al., *Arch Biochem Biophys*, 280(1):1–8 (1990).
Halliwell, *Biochem. Pharmacol.*, 37(4):569–571 (1988).
Harlow et al., A laboratory manual, Cold Spring Harbor Laboratory. Chapters 6 and 14 (1988).
Hayakawa, *J. Chromatography B*, 698:27–33 (1997).
Hedges et al., *Acad. Emerg. Med.*, 3:27–33 (1996).
Hisashi, "Atp–sensitive k+ channels in Pancreatic, Cardiac, and Vascular Smooth Muscle Cells," found at http://oac3.hsc.uth.tmc.edu/apstracts/1997/cell/October/291C.html, p. 1 (Oct. 1997), published in APStracts on Oct. 7, 1997.

Huang, "Ischemia– and Reperfusion–Sensitive Cardiac Sympathetic Afferents: Influence of Hydrogen Peroxide and Hydroxyl Radicals," found at http://www.uth.tmc.edu/apstracts/1995/heart/April/120th.html, p. 1 (Apr. 1995), published in APStracts on Apr. 4, 1995.
Ishikawa et al., *Clin Chem.*, 43(3):467–475 (1997).
Ishimoto, "Role of Oxygen–Derived Free Radicals in Fetal Growth Reardation Induced by Ischemia–Reperfusion in Rats," found at http://oac3.hsc.uth.tmc.edu/apstracts/1996/heart/September/37lh.html, p. 1 (Sep. 1996), published in APStracts on Sep. 19, 1996.
Kadota et al., *Japanese Circulation Journal*, 55:937–941 (1991).
Karck et al., *J Heart Lung Transplant*, 11:979–85 (1992).
Keller, *Chem. Res. Toxicol.*, 6(4):430–433 (1993).
Laussac et al., *Biochem*, 23:2832–2838 (1984).
Mangano et al., *N Engl J Med*, 323:1781–8 (1990).
Marx, *Biochem. J.*, 236:397–400 (1985).
Masuoka et al., *J. Biol. Chem.*, 268:21533–21537 (1993).
McCord et al., *N. Eng. J. Med.*, 312:159–163 (1985).
Meister & Anderson, Interconversion of Glutathione and Glutathione Disulfide, pp. 733–739.
"Metal–Binding Groups of Proteins: A. Evidence for Specific Donor Atoms," Chapter IV, pp. 61–99.
"New Marker for Exercise–Induced Ischemia" American Association for Clinical Chemistry, found at http://www.aacc.org/cin/profiles/97profiles/05/diagpro9702.html, (1997).
Nieboer et al., *Br. J. Ind. Med.*, 41:56–63 (1984).
Odeh, *N Eng. J Med*, 324(20):1417–1422 (1991).
Pepine et al., "Effects of Treatment on Outcome in Mildly Symptomatic Patients with Ischemia During Daily Life The Atenoloi Silent Ischemia Study (ASIST)," *Circulation*, 90:762–768 (1994).
Predki, *Biochem. J.*, 287:211–215 (1992).
QLT Phototherapeutics Inc., "Product Brochure: Photofrin" Manfactured by Lederle Parenterals, Inc. (Apr. 1996).
Quinlan et al., *J. Pharm. Sci.*, 81:611–614 (1992).
Reimer et al., "The Wavefront Phenomenon of Ischemic Cell Death 1. Myocardial Infarct Size v. Duration of Coronary Occlusion in Dogs.," *Circulation*, 56:786–793 (1977).
Reimer et al., Myocardial Ischemia, Hypoxia, and Infarction, The Heart and Cardiovascular System: Scientific Foundations, Raven Press (New York), pp. 1875–1953 (1992).
Roberts et al., *Clin. Lab. Med.*, 17(4):669–683 (1997).
Röth, *Acta Chirugica Hungarica*, 36(1–4):302–305 (1997).
Sadler et al., *Eur. J. Biochem.*, 226:193–200 (1994).
Sheat, *Clin. Chem.*, 37(7):1221–1224 (1991).
Shirakawa et al., *Clin Allergy*, 18:451–460 (1988).
Shirakawa et al., *Clin Exp Allergy*, 22:213–218 (1992).
Shirakawa et al., *Thorax*, 45:267–271 (1990).
Sogami, *Int. J. Peptide Protein Res.*, 24:96–103 (1984).
Stoh, *J. Basic & Clin. Physiol. & Pharmacol.*, 6(3–4):205–228 (1995).
Tucker, "Involvement of a Lysine Residue in the N–terminal Ni2+ and Cu2+ Binding Site of Serum Albumins, Comparison with Co2+, Cd2+ and Al3+, " found at http://search19.proxy.aol.com:800/post–query/MedLine/hrs1994/23450?albumin+n+t p. 1 (1994), Christopher Ingold Laboratories, University of London, England.
Stryker, *Biochemistry*, pp. 62–64 and 895–897 (3rd ed. 1988).
"Toxicity and Physicochemical Properties of Metal: Coordination and Chelation," Ch. 4, pp. 115–122.

Ueda et al., *Free Radic. Biol. Med.*, 18:929–933 (1995).
Veien et al., *Contact Dermatitis*, 5:378–382 (1979).
Venugopal and Luckey, "Metal Toxicity in Mammals: Chemical Toxicity of Metal and Metalloids," vol. 2, pp. 283–289 (1978).
Vogel et al., *Quant. Chem. Anal.*, 199–203.
Witko–Sarsat, *Kidney Int'l.*, 49:1304–1313 (1996).
Wysocki, *Coronary Artery Disease*, 4(7):645–647 (1993).
Yoon et al., *J. Surg Res*, 46:163–165 (1989).
Brennan et al., *Clin Chim. Acta*, 1988, 176:179–184.
Pepine et al., eds., *J. Myocard. Isch.*, 1994, 6(3):8–9.
Afanas'ev, Superoxide Ion: Chemistry and Biological Implications, CRC Press, Boca Raton, vol. 1, pp. 26–27, 51, 147–148, 168–195, 248–266.
Peter, Jr., All About Albumin, Biochemistry, Genetics and Medical Applications, Academic Press, San Diego. 1996. p. 244.
Lapresle (1988) Anal. Biochem. 174:308.
Herbert et al. eds. (1995) Dict. Of Immunol. p. 58.
Bal e tal.; "Multi–Metal Binding Site of Serum Albumin"; *Journal of Inorganic Biochemistry;* 1998; 70:33–39.
Buranaprapuk et al.; "Protein Cleavage by Transition Metal Complexes Bearing Amino Acid Substituents"; *Biochimica et Biophysica Acta;* 1998; 1387:309–316.
European Search Report dated Nov. 29, 2004, Issued by the European Patent Office for European Patent Application No. 99950055.6–1521–US9922746.
Apple et al. (2002) Clin. Chem. 48:10.
Bar–Or et al. (1999) "Reduction in the Cobalt Binding Capacity of Human Albumin with Myocardial Ischemia", Amer. Coll. Emerg. Physicians, Las Vegas, Sep. 1999.
Belch et al. (1989) Free Radic. Biol. Med. 6(4):375–378.
Berenshtein et al. (1997) J Mol Cell Cardiol. 29(11):3025–34.
Bradshaw et al. (1968) J. Biol. Chem. 243:3817–25.
Bradshaw et al. (1969) J. Biol. Chem. 244:5582–89.
Christenson et al. (2001) Clin. Chem. 47:464–70.
Dorland's Illustrated Medical Dict. (2002) pp. 911, 1275.
Cin et al. (1996) Int. J. Cardiol. 53:237–244.
Gryzunov et al. (2003) Arch. Biochem. Biophys. 413(1):53–56.
Morris et al. (2001) Eur. Heart J. Abs. Supp 22:608.
Wu et al. (2001) Cardiovascular Toxicol.1:147–151.
Wu, A. (2000) "The Albumin Cobalt Binding Test as a Marker of Cardiac Ischemia" at the Third Annual Joint Summit on Markers in Cardiology.
Anderson, "Effects of na+k=2ci Cotransport Inhibition on Mycardial NA and CA During Ischemia and Reperfusion," found at http://www.uth.tmc.edu/apstracts/1995/cell/September/319c.html. p. 1 (Sep. 1995), published in APStracts on Sep. 23, 1995.
Bautista et al., *Biosci. Biotechnol. Biochem.,* 62(3):419–423 (1998).
Braugher, "Calicum and Lipid Peroxidation," from Central Nervous System Diseases Research Unit, p. 99 (1987), The Upjohn Company, Kalamazoo, Michigan.
Chan, *Eur. J. Biochem.,* 227:524–528 (1995).
Cobbe, *J. Mol. Cell. Card.,* 12:745–760 (1980).
Cotelle et al., *J. Inoganic Biochem.,* 46:7–15 (1992).
"DNA Damage Linked to Risk of Breast Cancer Spread," found at http://www.psigroup.com/dg/6c2e.htm.
Das et al., *Meth. Enzymol.,* 233:610 (1994).
Davies, *J. Free Radicals Biol. & Med.* 2:155–173 (1988).

Davies, "Oxygen Radicals Stimulate Intracellular Proteolysis and Lipid Peroxdiation by Independent Mechanisms in Erythrocytes," from the Dept. of Physiology and Biophysics, Harvard Medical School, vol. 262, No. 17, issue of Jun. 15, pp. 8220–8225, (1987), Boston Massachusetts.
Davies et al., *J. Biological Chem.*, 262(20):9895–9901 (1987).
Davies et al., *J. Biological Chem.*, 262(20):9902–9907 (1987).
Davies et al., *J. Biological Chem.*, 262(20):9908–9913 (1987).
Davies et al., *J. Biological Chem.*, 262(20):9914–9920 (1987).
Gobel et al., *Eur. Heart J.*, 19:1208–1213 (1998).
Gomez, "Ruling Out Ischemia Saves Time and Money," vol. 6(9) pp. 148, 150, found at http://www.medscape.com/CPG/ClinRE. . . c0609.25.gomez/c0609.25.gomez.html, pp. 1–2, Clincians Publishing Group and Williams & Wilkins, (1996).
Gutteridge et al., *Biochim Biophys Acta*, 759:38–41 (1983).
Halliwell et al., *Arch Biochem Biophys*, 246(2):501–514 (1986).
Halliwell "Oxygen Radicals and Tissue Injury," Proceedings of Brook Lodge Symposium, pp. 100–104 (Apr. 1987), Augusta, Michigan.
Halliwell et al., *Arch Biochem Biophys*, 280(1):1–8 (1990).
Halliwell, *Biochem. Pharmacol.*, 37(4):569–571 (1988).
Harlow et al., A laboratory manual, Cold Spring Habor Laboratory. Chapters 6 and 14 (1988).
Hayakawa, *J. Chromatography B*, 698:27–33 (1997).
Hedges et al., *Aced, Emerg. Med.*, 3:27–33 (1996).
Hisashi, "Atp–sensitve k+channels in Pancreatic, Cardiac, and Vascular Smooth Muscle Cells," found at http://oac3.hsc.uth.tmc.edu/apstracts/1997/cell/October/291C.html, p. 1 (Oct. 1997), published in APStracts on Oct. 7, 1997.
Huang, "Ischemia–and Reperfusion–Sensitive Cardiac Sympathetic Afferents: Influence of Hydrogen Peroxide and Hydroxyl Radicals," found at http://www.uth.tmc.edu/apstracts/1995/heart/April/120th.html, p. 1 (Apr. 1995), published in APStracts on Apr. 4, 1995.
Ishikawa et al., *Clin. Chem.*, 43(3):467–475 (1997).
Ishimoto, "Rote of Oxygen–Derived Free Radicals in Fetal Growth Reardation Induced by Ischemia–Reperfusion in Rats," found at http://oac3.hsc.uth.tmc.edu/apstracts/1996/heart/September/37th.html, p. 1 (Sep. 1996), published in APStracts on Sep. 19, 1996.

Kadota et al., *Japanese Circulation Journal*, 55:937–941 (1991).
Keller, *Chem. Res. Toxicol.*, 6(4):430–433 (1993).
Laussac et al., *Biochem*, 23:2832–2838 (1984).
Marx, *Biochem, J.*, 236:397–400 (1985).
Masuoka et al., *J. Biol. Chem.*, 268:21533–21537 (1993).
McCord et al., *New England Journal Of Medicine*, 312:159–163 (1985).
"New Marker for Exercise–Induced Ischemia" American Association for Clinical Chemistry, found at http://www.aaoc.org/cin/profiles/97profiles/05/diagpro9702.html, (1997).
Pepine et al., "Effects of Treatment on Outcome in Mildly Symptomatic Patients with Ischemia During Daily Life The Atenoiol Silent Ischemia Study (ASIST)," 90:762–768 (1994).
Predki, *Biochem. J.*, 287:211–215 (1992).
QLT Phototherapeutics Inc., "Product Brochure: Photofrin" Manufactured by Lederle Parenterals, Inc. (Apr. 1996).
Quintan et al., *J. Pharm. Sci.*, 81:611–614 (1992).
Reimer et al., "The Wavefront Phenomenon of Ischemic Cell Death 1. Myocardial Infarct Size v. Duration of Coronary Occlusion in Dogs.," *Circulation*, 56:786–793 (1977).
Reimer et al., "Myocardial Ischemia, Hypoxia, and Infraction," The Heart and Cardiovascular System: Scientific Foundations, Raven Press (New York), pp. 1875–1953 (1991).
Roberts et al., *Clin. Lab. Med.*, 17(4):669–683 (1997).
Röth, *Acta Chinugica*, 36(1–4):302–305 (1997).
Sadler et al., *Eur. J. Biochem.*, pp. 193–200 (1994).
Sheat, *Clin. Chem.*, 37(7):1221–1224 (1991).
Sogami, *Int. J. Peptide Protein Res.*, 24:96–103 (1984).
Stohs, *J. Basic & Clin. Physiol. & Pharmacol.*, 6(3–4):205–228 (1995).
Tucker, "Involvement of a Lysine Residue in the N–terminal Ni2+and Cu2+ Binding Site of Serum Albumins, Comparsion with Co2+, Cd2+ and Al3+," found at http://search19.proxy.aol.com:8000/post–query/MedLine/hrs1994/23450?albumin+n+l p. 1 (1994), Christopher Ingold Laboratories, University of London, England.
Ueda et al., *Free Radic. Biol. Med.*, 18:929–933 (1995).
Vogel et al., *Quant. Chem. Anal.*, 199–203.
Witko–Sarsat, *Kidney Int'l.*, 49:1304–1313 (1996).
Wysocki, *Coronary Artery Disease*, 4(7):645–647 (1993).

* cited by examiner

MARKER USEFUL FOR DETECTION AND MEASUREMENT OF FREE RADICAL DAMAGE AND METHOD

CROSS REFERENCE TO RELATED APPLICATION

The present application is a continuation of pending PCT application PCT/US99/22746, filed Oct. 1, 1999, which is a continuation-in-part of U.S. application Ser. No. 09/165,961, filed Oct. 2, 1998, now U.S. Pat. No. 6,475,743; the entire contents of both of which are incorporated herein by this reference. PCT application PCT/US99/22746 claims priority from U.S. application Ser. No. 09/165,961 and from U.S. provisional application Ser. No. 60/102,962, also filed on Oct. 2, 1998.

FIELD OF THE INVENTION

The present invention relates to a marker for detecting and measuring free radical damage. The invention also relates to methods and materials for the detection and measurement of the damaging activity of free radicals.

BACKGROUND OF THE INVENTION

Free radicals are atoms or groups of atoms with an odd (unpaired) number of electrons and can be formed when oxygen interacts with certain molecules. Once formed these highly reactive radicals can start a chain reaction, like dominoes. Their chief danger comes from the damage they can do when they react with important cellular components such as DNA, or the cell membrane. Cells may function poorly or die if this occurs.

A free radical is any molecular species capable of independent existence, that contains one or more unpaired valence electrons not contributing to intramolecular bonding, and is—in that sense—"free". Free radicals are produced by oxidation/reduction reactions in which there is a transfer of only one electron at a time, or when a covalent bond is broken and one electron from each pair remains with each atom. Free radicals are highly reactive, owing to the tendency of electrons to pair—that is, to pair by the receipt of an electron from an appropriate donor or to donate an electron to an appropriate acceptor. Thus, once formed, free radicals initiate a chain reaction, like dominoes—whenever a free radical reacts with a non-radical, a chain reaction is initiated until two free radicals react and then terminate the propagation with a 2-electron bond (each radical contributing its single unpaired electron).

In biological systems free radicals have a range of transitory existences depending upon their reactivity. Some are stable, e.g. melanins can have a long lifetime, moderately stable ones such as nitric oxide can have lifetimes of ~5 seconds and highly unstable ones such as hydroxyl radicals exist for only a hundredth of a microsecond. The chief danger of free radicals is the damage they can do when they react with important cellular components, such as DNA or the cell membrane. The result of the action by free radicals on cells can be diminished or impaired cellular functioning or even cell death. For instance, oxygen-free radicals are believed to play a significant role in the aging process. These free radicals often take an electron away from a "target" molecule to pair with their single free electron. This process is referred to as "oxidation" and is a known cause of cellular damage and death. Oxygen-free radicals are also implicated in many diseases including neurodegenerative diseases (ALS, Parkinson's, Alzheimer's), cataractogenesis, atherosclerosis, diabetes mellitus, ischemia-reperfusion injury, kwashiorkor, and certain toxicities, to mention only a few.

There are many sources of free radicals both within and external to cells. Free radicals are produced by normal ongoing metabolism, especially from the electron transport system in the mitochondria and from a number of normally functioning enzymes, such as xanthine oxidase, cytochrome p450, monoamine oxidase, and nitric oxide synthase. In the brain, free radicals are produced from the autoxidation of norepinephrine and dopamine. The autoxidation of catechols to quinones generates reduced forms of molecular oxygen, sources of free radicals (e.g., superoxide and hydrogen peroxide). One study suggests that oxidants generated by mitochondria are the major source of oxidative lesions that accumulate with age. See Ames, B. N., M. K. Shigenaga and T. M. Hagen, "Oxidants, antioxidants, and the degenerative diseases of aging." *Proc. Natl. Acad. Sci. USA* 90: 7915–7922 (1993).

Free radicals also function beneficially in normal physiology, including information processing in the brain. Since free radicals can donate an electron to an appropriate acceptor ("reduction reaction") or pair their unpaired electron by taking one from an appropriate donor ("oxidation reaction") they have major influences on the so-called "redox state" in cells—important in normal physiological regulatory reactions. Major free radical targets are molecular complexes that readily give up or acquire a single electron, e.g., those with sulfhydryl/disulfides or with paramagnetic metals (iron, copper). It is calculated that endogenously generated oxygen free radicals make about 10,000 oxidative interactions with DNA per human cell per day (Ames et al., 1993, supra).

Under normal conditions the damaging actions of oxygen free radicals are minimized by abundant protective and repair mechanisms that cells possess, including many enzymes (e.g. superoxide dismutase, catalase) and redox active molecules (e.g., glutathione, thioredoxin).

There is currently an overwhelming need for a sensitive test of free radical damage. For instance, it has been found that the DNA in breast cancer tumors that have generated metastases contain more than twice the amount of free radical damage than tumors that remained confined to the breast. The ability to detect this free radical damage would allow identification of an identifiable metastatic pattern or "profile," which would be of great benefit in determining if newly diagnosed breast cancer was likely to spread and whether aggressive radiation and chemotherapy is needed. See, e.g., Malins D. et al., "Progression of Human Breast Cancers to the Metastatic State Is Linked to Hydroxyl Radical-induced DNA Damage," *Proc. Natl. Acad. Sci. USA* 93:2557–2563 (1996). However, no viable test exists.

There currently exists several limited methods for detection of the damaging activity of free radicals in the body. One method uses an isoprostane called IPF2alpha-1, an abundant and stable byproduct of free-radical catalyzed oxidation of arachidonic acid, which is easily detected in urine. Arachidonic acid is a fatty molecule found in cell membranes throughout the body. Pratico D. et al., "Localization of distinct F2-isoprostanes in human atherosclerotic lesions," *J. Clin. Invest.* 100(8)2028–2034 (1997). Other methods take advantage of the formation of carbonyls from lipids, proteins, carbohydrates, and nucleic acids during oxidative stress. For example, metal-catalyzed, "site-specific" oxidation of several amino acid side-chains has been reported to result in the production of aldehydes or ketones, and peroxidation of lipids to generate reactive aldehydes such as malondialdehyde and hydroxynonenal. These oxidative changes have been detected in situ using 2,4-dinitrophenylhydrazine labeling linked to an antibody system specific to localized biomacromolecule-bound carbonyl reactivity. See
Smith, M. A. et al., "Cytochemical demonstration of oxidative damage in Alzheimer disease by immunochemical enhancement of the carbonyl reaction with 2,4-dinitrophenylhydrazine," *J Histochem. Cytochem.* 46(6) :731–735 (1998). Use of immunochemical assays for detection of carbonyl moieties resulting from oxidative damage to bovine serum albumin has also been reported. See Keller, R. J. et al., "Immunochemical detection of oxidized proteins," *Chem. Res. Toxicol.* 6(4): 430433 (1993), and Mateos-Nevado, D. J., "Immunological detection and quantification of oxidized proteins by labeling with digoxigenin," *Biosci. Biotechnol. Biochem.* 62(3):419–423 (1998).

These methods, however, are limited in their usefulness and applicability due to the highly specific and system-limited nature of the markers utilized for detection. The present invention, in contrast, provides a marker for the existence and detection and/or measurement of free radical damage which is highly sensitive and present in a majority of human fluids and tissues.

SUMMARY OF THE INVENTION

The need for rapid, immediate and continuous detection of free radical damage, locally or systemically, is met by the present invention. The present invention provides a marker for the detection of free radical damage. The marker is modified albumin, wherein the albumin is modified in a manner which results in inhibition of the metal binding capacity of the N-terminus of albumin.

The invention also provides a method for detecting and quantifying the marker. The method comprises contacting a biological sample containing albumin with an excess quantity of a metal ion salt, the metal ion of which is capable of binding to the N-terminus of unmodified albumin. As a result of this contacting, a mixture of bound metal ions and unbound metal ions is formed. In one embodiment, the quantity of the bound metal ions is measured directly. In another embodiment, the excess quantity of the metal ion salt is a predetermined quantity, and the quantity of unbound metal ions is determined and used to determine the quantity of bound metal ions. By whichever of these methods it is determined, the quantity of the bound metal ions is correlated to a known value to determine the quantity of the marker present in the sample and if the quantity of the marker is sufficient to indicate free radical damage.

The invention provides another method for detecting and quantifying the marker. This method comprises determining the quantity of copper ions present in a purified albumin sample. This quantity is then correlated with a known value to determine the quantity of the marker present in the sample and if the quantity of the marker is sufficient to indicate free radical damage.

The invention further provides a compound having the formula Asp-Ala-His-Lys-R. R is any chemical group capable of providing a detectable signal when the compound is bound to a metal ion capable of binding to the N-terminus of unmodified human albumin.

The invention also provides antibodies and immunoassays. In particular, the invention provides an antibody that binds specifically to the marker and an antibody that binds specifically to the peptide Asp Ala His Lys [SEQ ID NO:1] having a metal ion bound thereto. The immunoassays include immunoassays employing one of these two antibodies and an immunoassay employing the marker as an antigen.

Finally, the invention provides kits for detecting or quantitating the marker. In one embodiment, the kit comprises a container holding a metal ion salt and a container holding a peptide having the sequence Asp Ala His Lys [SEQ ID NO:1]. In a second embodiment, the kit comprises a container holding a compound of the formula Asp-Ala-His-Lys-R, where R is a group capable of producing a detectable signal when a metal ion that is capable of binding to the N-terminus of unmodifed albumin is bound to the compound. In a third embodiment, the kit comprises a container holding an antibody that binds specifically to the peptide Asp Ala His Lys [SEQ ID NO:1] having a metal ion bound thereto. In a fourth embodiment, the kit comprises an antibody that binds specifically to the marker.

The marker may be used as a "biochemical tag," thereby allowing for sensitive detection and measurement of the efficacy of clinical drugs and therapeutics which result in the generation of free radicals, such as Photofrin® (porfimer sodium), or which act to limit free-radical damage, such as free radical scavengers. The marker also acts as a "biological tag" of a process implicated in a wide array of conditions, diseases and sequelae and, accordingly, may be used to monitor such conditions, diseases and sequelae and their treatment.

Additional advantages, applications, embodiments and variants of the invention are included in the Detailed Description Of The Presently-Preferred Embodiments Of The Invention and Examples sections.

DETAILED DESCRIPTION OF THE PRESENTLY-PREFERRED EMBODIMENTS

The present invention provides a marker useful for detection and measurement of free radical damage. Specifically, the invention takes advantage of alterations which occur to the N-terminus of the human albumin molecule in the presence of free radicals. These alterations effect the ability of the N-terminus of the albumin molecule to bind metals.

Human serum albumin ("HSA") is the most abundant protein in blood (40 g/l) and the major protein produced by the liver. Many other body fluids also contain albumin. The main biological function of albumin is believed to be regulation of the colloidal osmotic pressure of blood. The amino acid sequence and structure of human albumin have been determined. Specifically, human albumin is a single polypeptide chain consisting of 585 amino acids folded into three homologous domains with one free sulfhydryl group on residue # 34, having a specific amino acid content as follows:

Bases: Asp Asn Thr Ser Glu Gin Pro Gly Ala Cys Val Met Ile Leu Tyr Phe His Lys Trp Arg Residues 39 15 30 22 60 23 25 12 63 35 39 6 8 61 18 30 16 58 1 23

The N-terminus of albumin is known to possess metal binding capacity (see Chan et al., "Site-specific N-terminal auto-degradation of human serum albumin," *Eur. J. Biochem.* 277, 524–528 (1995)). Damage to the structure of albumin resulting from the binding of metals such as vanadium, copper and iron has been detected by changes to the thiol groups and the tryptophan residue (Quinlan et al., "Vanadium and copper in clinical solutions of albumin and their potential to damage protein structure," *J. Pharm. Sci.*, 81, 611–614 (1992)). Additionally, oxidative modifications to structure of bovine serum albumin have been noted generally, but not within the N-terminus as in the present invention. See Davies et al., "Protein damage and degradation by oxygen radicals," *J. Biol. Chem.* 262, 9895–9901, 9908–9913 (1987); Marx, G. et al., "Site-specific modification of albumin by free radicals. Reaction with copper(II) and ascorbate," *Biochem. J.* 236(2):397–400 (1986).

The present invention takes advantage of the discovery by the present inventors of the previously unknown phenomenon that modifications to the structure of human serum albumin caused by free radicals occur within the N-terminus such that metal binding with the N-terminal metal binding site is effectively precluded. While not being bound by any particular theory, it is believed that a combination of separate phenomena explain the mechanism by which the presence of free radicals causes an alteration of the N-terminus of albumin resulting in a loss of metal-binding capacity. First, it is believed that the alteration may be due to the loss of a proton on the backbone of the alanine residue causing cyclization of the aspartate carboxyl group with the alanine carbon. Cyclization such as this one has been reported previously for albumin, as an autodegradation process with heat at 57 degrees Celsius. See Chan et al., 1995, supra. Applicants, believe that the cyclization process is accelerated in the presence of free radicals. Second, it is possible that free radicals cause the clipping of the two N-terminal amino acids (aspartate-alanine) from the N-terminal of albumin and that the cleaved dipeptide undergoes cyclization. Third, it is known that metal ions are released from their storage sites during injury and other events that result in free radical formation. See, e.g., Roth, *Acda Chir. Hung.*, 36 302–305 (1997). One of these metal ions is copper which binds with high affinity to the N-terminal binding site of albumin. Thus, the binding of copper to the N-terminal binding site could effectively "alter" the N-terminus, preventing binding of other metal ions to this site. Regardless of the underlying mechanism, the effect of free radicals on the N-terminus of albumin is discovered to be a loss of metal binding capacity.

As used herein, the "N-terminus of albumin" refers to a portion of the albumin molecule comprising the N-terminal metal binding site. In human albumin, the N-terminal binding site has the sequence Asp Ala His Lys [SEQ ID NO:1], which are the four N-terminal amino acids of human albumin.

As used herein, the terms "unmodified albumin" and "naturally-occurring albumin" mean albumin on which the N-terminal binding site is unaltered. Thus, "unmodified albumin" and "naturally-occurring albumin" are able to bind metal ions to the N-terminal binding site to the full extent possible.

As discussed above, the "marker" of the invention is albumin modified so that binding to the N-terminal metal binding site is inhibited (i.e., reduced or totally precluded).

The marker will be present in biological samples that normally contain albumin. Biological samples containing albumin are well known in the art. Preferably, the biological sample is plasma, serum, cerebrospinal fluid, or albumin purified from these sources. Methods of obtaining biological samples are well known in the art. Methods of purifying albumin are also well known in the art and include electrophoresis, ion exchange chromatography, affinity chromatography, gel filtration and others. "Purified albumin" includes partially purified albumin (at least 70% pure) and albumin purified to homogeneity.

In one embodiment of the invention, the biological sample is contacted with an excess quantity of a metal ion salt, the metal ion of which is capable of binding to the N-terminus of naturally occurring human albumin. "Excess quantity" means an amount of the metal ion salt that is substantially greater than is stoichiometrically required to bind all of the available albumin metal binding sites expected to be present in the biological sample. Such quantities can be determined empirically and making such determinations is within the skill in the art. The contacting takes place under conditions effective so that the metal ions can bind to the N-terminal binding sites of unmodified albumin. Such conditions include the time, temperature, and pH. Sufficient and optimal conditions can be determined empirically and making such determinations is within the skill in the art. Preferably, the metal ion salt is a salt of a transition metal ion of Groups 1b-7b or 8 of the Periodic Table of the elements. Also preferred is a salt of a metal selected from the group consisting of V, As, Co, Sb, Cr, Mo, Mn, Ba, Zn, Ni, Hg, Cd, Fe, Pb, Au, Cu and Ag. Most preferably, the metal ion salt is a cobalt salt.

As a result of contacting the biological sample and the metal ion salt, a mixture containing bound metal ions and unbound metal ions is formed. The amount of the bound metal ions can be measured directly. This can be accomplished in a number of ways. For instance, the bound metal ions can be quantitated by absorption spectroscopy, atomic emission spectroscopy or by an immunoassay. Also, nuclear magnetic resonance can be used to quantitate some metal ions (e.g., nickel). To perform the immunoassay, an antibody, preferably a monoclonal antibody, that binds specifically to the N-terminus of albumin to having the metal ion to be used in the assay bound to the N-terminal binding site is contacted with the mixture of bound and unbound metal ions. Preferably the antibody binds specifically to the peptide Asp Ala His Lys [SEQ ID NO:1] having bound thereto the metal ion to be used in the assay. Methods of making antibodies and performing immunoassays are well known in the art, and sufficient and optimal conditions are known in the art or can be determined empirically, and making such determinations is within the skill in the art. The bound metal ions may optionally be separated from the unbound metal ions before measuring the bound metal ions. The bound metal ions can be separated in a number of ways. For instance, they could be separated by contacting the mixture of bound and unbound metal ions with an antibody specific for albumin coupled to a solid phase.

Alternatively, the quantity of unbound metal ions in the mixture can be measured. To do so, a predetermined amount of the metal ion salt must be contacted with the biological sample. Using the known predetermined amount of metal ion salt and the measured amount of unbound metal ions, the amount of bound metal ions can be calculated. Of course, controls to account for background and for losses due to sample handling must be employed.

Measurement of the unbound metal ions can be accomplished in a number of ways.

For instance, the unbound metal ions can be quantitated by absorption spectroscopy or atomic emission spectroscopy.

In addition, the mixture of bound metal ions and unbound metal ions can be contacted with the peptide Asp Ala His Lys [SEQ ID NO:1] so that the unbound metal ions in the mixture bind to this peptide. The unbound metal ions can first be separated from the bound metal ions, after which the unbound metal ions are contacted with the peptide. Also, since an excess quantity of the metal ion salt is used, only a portion of the mixture or of the separated unbound metal ions will generally be used to perform the assay. The metal ions bound to the peptide can be detected in a number of ways, e.g., by absorption spectroscopy or atomic emission spectroscopy or by means of an immunoassay as described above. In the case of the immunoassay, if the unbound metal ions are not separated from the bound metal ions before adding the peptide to the unbound metal ions, the metal ions bound to the peptide must be separated from the mixture before they can be detected.

In another preferred embodiment, the mixture of bound metal ions and unbound metal ions is contacted with the compound Asp-Ala-His-Lys-R. The compound is capable of binding the unbound metal ions in the mixture, and R is a group capable of producing a detectable signal when the compound is bound to any metal ion capable of binding to the N-terminal binding site of naturally occurring human albumin. The signal produced by R is detected to determine the quantity of unbound metal ions present in the mixture. The unbound metal ions may be separated from the bound metal ions before the unbound metal ions are contacted with the compound. Also, since an excess quantity of the metal ion salt is used, only a portion of the mixture or of the separated unbound metal ions will generally be used to perform the assay. R may be a polymer or other substance having a physical or chemical characteristic that changes when a metal ion binds to the compound (e.g., causing a small current change or other detectable change). R may also be a fluorescent, chemiluminescent or radioactive label, an enzyme that reacts with a substrate to produce a detectable signal, or any of the other well known labels typically used for detection purposes in immunoassays. Preferably R is a fluorescent label or an enzyme. The signal produced by R may be detected in a number of ways. Preferably, it is detected spectrophotometrically. To detect the signal produced by R, it may be necessary to separate the compound having metal ions bound to it from the compound not having metal ions bound to it. This can be accomplished in a number of ways. For instance, an antibody specific for Asp Ala His Lys [SEQ ID NO:1] having, or not having, the metal ion bound to it coupled to a solid phase can be used.

When the metal ion salt is a salt of a metal selected from the group consisting of V, As, Co, Sb, Cr, Mo, Mn, Ba, Zn, Ni, Hg, Cd, Fe, Pb, Au, Cu and Ag, the unbound metal ions can be quantitated by contacting the mixture of bound and unbound metal ions, or a portion thereof, with an aqueous solution of a color forming compound that is capable of producing a color when bound to one of these metal ions. As a result of the addition of the color forming compound, a colored solution is formed. The color intensity of the colored solution can be measured in any of several ways well known in the art. Preferably, the color intensity is measured spectrophotometrically. Preferred embodiments of this method include the additional step of diluting the colored solution with an aqueous solution isosmotic with blood serum or plasma (e.g., physiological saline) prior to determining the color intensity. Preferred color forming compounds are dithiothreitol, ferrozine N,N,N,'N'-tetrakis(2-pyridylmethyl) ethylene diamine), and the compound Asp-Ala-His-Lys-R', wherein R' is any group capable of producing a color when the compound is bound to a metal ion capable of binding to the N-terminal binding site of albumin. Preferably R' is an enzyme that reacts with a substrate to produce a color. Other suitable color forming compounds are known in the art. See U.S. Pat. Nos. 5,227,307 and 5,290,519. Most preferably, the color forming compound is ferrozine. Also preferably, this method is performed in a pH range of 7 to 9. A preferred metal ion salt is a cobalt salt.

In another embodiment of the invention, the occurrence or non-occurrence of the marker is detected by detecting the amount of copper ions present in a purified albumin sample, and correlating the quantity of copper ions present with a known value to determine the quantity of the marker present in the sample and if the quantity of the marker is sufficient to indicate free radical damage. Preferred methods for detection of the amount of copper ions present in the purified albumin sample are by atomic absorption, atomic emission spectroscopy and immunological assay. A preferred method of conducting said immunological assay uses an antibody that binds specifically to an antigen comprising the peptide Asp-Ala-His-Lys [SEQ ID NO:1] having copper bound thereto.

Finally, the marker can be detected directly. This can be accomplished by an immunoassay employing an antibody that binds specifically to the marker.

The amount of bound metal ions is then correlated to a known value to determine the quantity of the marker present in the biological sample and if the quantity is sufficient to indicate free radical damage. This is done by comparing the amount of bound metal ions in the patient sample to the amount of bound metal ions found in normal individuals. "Normal individuals" are those not suffering from a disease or condition in which free radicals play a role. For instance, the amount of bound metal ions can be compared to a normal range. This normal range is found by determining the amount of bound metal ions in a large number of samples from normal individuals by the same method (i.e., same type of biological sample, same steps, same reagents, same conditions, etc.) as used for the patient sample. If the amount of bound metal ions is outside the normal range, then free radical damage is indicated. Alternatively, the amount of bound metal ions can be compared with a cut-off value which is indicative of free radical damage. The cut-off value can be determined by u testing a large number of samples from normal individuals and from patients known to be suffering free radical damage or suffering from a specific disease or condition of interest in which free radicals are known to play a role. If the amount of bound metal ions exceeds the cut-off, then free radical damage is indicated. In analyzing data, including determining a normal range or a cut-off value, standard statistical methods well known in the art are employed. Finally, as can be appreciated, the normal ranges and the cut-off values can be expressed in the units of detection (e.g., levels of absorbance or of fluorescence) as a matter of convenience and ease of making the correlation.

The methods of the invention can be used to monitor and assess diseases and conditions in which free radicals play a role. These diseases and conditions include adult respiratory distress syndrome, aging, artherosclerosis, arthritis, asthma, autoimmune diseases, cancer, carcinogenesis, cellular damage caused by ionizing radiation (e.g., radiation of tumors), chronic granulomatous disease, cirrhosis, Crohn's disease, degenerative eye diseases (e.g., cataracts and macular degeneration), diabetes, diabetic retinopathy, emphysema, inflammation, ischemia, neoplastic diseases, neurological trauma, neurodegenerative diseases (e.g., Alzheimer's disease, Parkinson's disease, multiple sclerosis, and senile dementia), reperfusion, shock, tissue damage occurring upon administration of chemotherapeutics, tissue damage after surgery (e.g., transplantation surgery, open heart surgery, and any surgery where the blood supply to a tissue is cut off), and toxic reactions (e.g, herbicide, metal and antibiotic toxicities). See Manso, *Rev. Port. Cardiol.*, 11, 997–999 (1992); Florence, *Aust. N Z J. Opthalmol.*, 23, 3–7 (1992); Stohs, *J. Basic Clin. Physiol. Pharmacol.*, 6, 205–228 (1995); Knight, *Ann. Clin. Lab. Sci.*, 25, 111–121 (1995); Kerr et al., Heart & Lung, 25, 200–209 (1996).

The methods of the invention can also be used to monitor and assess the effectiveness of treatments of these diseases and conditions. These treatments can include standard treatments for the particular disease or condition. Alternatively, the treatment can be the use of a free radical scavenger to reduce free radical production and/or accumulation. Free radical scavengers include superoxide dismutase, catalase, glutathione peroxidase, ebselen, glutathione, cysteine, N-acetyl cysteine, penicillamine, allopurinol, oxypurinol, ascorbic acid, α-tocopherol, Trolox (water-soluble α-tocopherol), β-carotene, fatty-acid binding protein, fenozan, probucol, cyanidanol-3, dimercaptopropanol, indapamide, emoxipine, dimethyl sulfoxide, and others. See, e.g., Das et al., *Methods Enzymol.*, 233, 601–610 (1994); Stohs, *J. Basic Clin. Physiol. Pharmacol.*, 6, 205–228 (1995).

For instance, a patient undergoing surgery (e.g. open-heart surgery or surgery to transplant an organ into the patient) can be monitored for free radical damage prior to, during and after the surgery. If the marker is detected in sufficient quantities to indicate that free radical damage is occurring, then the patient can be treated to reduce the free radical damage (e.g., by administration of a free radical scavenger). This treatment can, in turn, be monitored to determine its effectiveness. If the treatment is shown to be ineffective, then corrective action can be taken. For instance, the dose of the compound being administered can be increased or a different treatment can be employed.

As another example, a patient undergoing radiation therapy (e.g., radiation for a tumor or prior to a bone marrow transplant) can be monitored prior to, during and after the radiation treatment. If the marker is detected in sufficient quantities to indicate free radical damage is occurring, then the patient can be treated to reduce the free radical damage, and this treatment can be monitored and changed if it proves ineffective.

As a further example, reperfusion of an ischemic tissue or organ (e.g., prior to and/or simultaneously with angioplasty or treatment with clot dissolving drugs, such as tissue plasminogen activators) can be monitored prior to, during and after the reperfusion. If the marker is detected in sufficient quantities to indicate that free radical damage is occurring, then the patient can be treated to reduce the free radical damage, and this treatment can be monitored and changed if it proves ineffective.

The methods of the invention can also be used to assess the type of therapy to be administered to a patient. For instance, the presence of free radical damage may indicate that a particular disease or condition (e.g., breast cancer) will be more serious than in the absence of free radical damage. This, in turn, may suggest that more aggressive or different treatment of the disease or condition is called for.

In addition, the methods of the invention can be used to detect free radical damage in an excised tissue or organ. If the marker is detected in sufficient quantities to indicate that free radical damage has occurred, the tissue or organ can be discarded as unsuitable for transplantation into a recipient or for research purposes (e.g., using a perfused liver to screen drugs).

The methods of the invention can also be used assess the clinical efficacy of drugs that produce free radicals. Such drugs include photosensitizing agents (and light-activated compounds) used in photodynamic therapy for the treatment of tumors, such as Photofrin® (porfimer sodium). In this procedure, a photosensitizing chemotherapeutic agent is injected into the blood stream, followed by application of low energy, non-thermal laser light 40 to 50 hours after injection, directly to the vicinity of the tumor. The laser light in combination with the photosensitizing agent, which is retained at much higher concentrations in the tumor tissue than normal tissue, causes destruction of the tumor cells. Normal tissues remain virtually untouched. Detection of the existence of the marker, and a corresponding change in the level thereof during the application of the laser, provides a indication (and allows for quantitation) of the effectiveness of the photodynamic therapy. Any of the methods described above allow for detection and measurement of the marker. For instance, a metal ion salt may be mixed with a purified albumin sample obtained from a patient serum, plasma, fluid or tissue sample. The metal ion salt will not bind with the marker due to the alteration of the binding site of the N-terminus. Accordingly, the existence and concentration of the marker can be determined by detection of the presence and quantity of bound or unbound metal ion. Measurement can be conducted by atomic absorption, infrared spectroscopy, or HPLC or other standard or non-standard methods, including radioactive immunoassay techniques.

The invention further provides kits for detecting and/or quantitating the marker. The kit is a packaged combination of one or more containers holding reagents and other items useful for detecting and/or quantitating the marker. The kit may comprise a container holding a metal ion salt and a container holding a peptide having the sequence Asp Ala His Lys [SEQ ID NO:1]. In an alternative embodiment, the kit may comprise a container holding a compound of the formula Asp-Ala-His-Lys-R, where R is defined above. This kit may further comprise another container holding a metal ion salt In yet another embodiment, the kit may comprise a container holding an antibody that binds specifically to the peptide Asp Ala His Lys [SEQ ID NO:1] when it has a metal ion bound thereto. This kit may further comprise another container holding a metal ion salt In a further embodiment, the kit may comprise a container holding an antibody that binds specifically to the marker. This kit may further comprise another container holding a metal ion salt. Suitable containers include microtiter plates, jars, vials, test tubes, syringes, and other containers known in the art. The kit may also contain other items which are known in the art and which may be desirable from a commercial and user standpoint, such as diluents, buffers, reagents, standards, empty syringes, instructions, etc.

The following additional abbreviations are utilized herein to refer to the following amino acids:

| Amino acid | Three-letter abbreviation | Single-letter notation |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |

-continued

| Amino acid | Three-letter abbreviation | Single-letter notation |
|---|---|---|
| Threonine | Thr | T |
| Tryptophan | Trp | W |
| Tyrosine | Tyr | Y |
| Valine | Val | V |

Finally, it is noted that a separate test method for ischemia using the marker of the present invention is described by the inventors herein in pending U.S. patent application Ser. Nos. 09/165,926 and 09/165,581, (both titled "TEST FOR RAPID EVALUATION OF ISCHEMIC STATES AND KIT"), filed Oct. 2, 1998, by the inventors herein (Bar-Or and Lau) in conjunction with inventor J. Winkler, both of which are herein incorporated by reference in their entireties. Another test for ischemia based on the detection of metal ions is described in U.S. Pat. Nos. 5,227,307 and 5,290,519, both of which are incorporated herein by reference in their entireties.

A greater understanding of the present invention and of its many advantages may be had from the following examples, given by way of illustration. The following examples are illustrative of some of the methods, applications, embodiments and variants of the present invention. They are, of course, not to be considered in any way limitative of the invention. Numerous changes and modification can be made with respect to the invention with departing from the spirit or scope of the invention.

EXPERIMENTS

In Vitro Models

An in vitro experimental model was conducted using an octapeptide having the same eight amino acid sequence as the N-terminus of human albumin. The following preliminary experiments (Nos. 1 through 11) demonstrate the properties and critical characteristics of the peptide probe.

EXAMPLE 1

Measurement of Cobalt Binding to HSA and Octapeptide Using Cold Cobalt Binding Assay OBJECTIVE: To investigate cobalt binding to the octapeptide and human serum albumin using cold cobalt binding assay.

EXPERIMENTAL: Octapeptide synthesized at the Inorganic Chemistry Department (BAM 1, Pat Ingrey, Cambridge): $NH_2$-Asp-Ala-His$^+$-Lys$^+$-Ser-Glu-Val-Ala-$CONH_2$ [SEQ ID NO:2]. Molecular weight: 855.4 Da.

SOLUTIONS: $CoCl_2$ 0.1% (w/v)=4.2 mM; HSA 3% (w/v)(in 75 mM HEPES pH 7.4)=0.45 mM; Octapeptide 0.965 mM (in 75 mM HEPES pH 7.4); HEPES 75 mM pH 7.4; DTT 0.15% (w/v); NaCl 0.85% (w/v)

METHOD: Two sets of two tubes each containing 200 μL of (a) 75 mM HEPES, pH 7.4, (b) 0.45 mM HSA in HEPES, or (c) 0.965 mM Peptide in HEPES, were added 50 μL $CoCl_2$ 0.1%. The tubes were allowed to stand at room temperature for 10 minutes. Then, 50 μL DTT 0.15% were added to one tube (test tube) and distilled $H_2O$ was added to the other (control tube) of each set, followed by standing for 2 minutes at room temperature. Then, 1 ml NaCl 0.85% was added, and the absorbance at 470 nm of the test tube versus the blank was measured.

Results:

| ID | A470 nm | | mean A470 | % bound |
|---|---|---|---|---|
| 75 mM HEPES pH 7.4 | 1.087 | 1.083 | 1.085 | 0.0 |
| 0.45 mM HSA in HEPES, pH 7.4 | 0.668 | 0.643 | 0.656 | 39.5 |
| 0.965 mM Peptide in HEPES, pH 7.4 | 0.638 | 0.655 | 0.647 | 40.4 |

CONCLUSIONS: Under the conditions used for the binding measurements, this experiment showed that: 1. Cobalt binds to the octapeptide (N-Asp-Ala-His$^+$-Lys$^+$-Ser-Glu-Val-Ala [SEQ ID NO:2]); 2. However, the octapeptide (0.965 mM) binds cobalt with a stoichiometry of 1:2.3.

EXAMPLE 2

Mass Spectrometry of Octapeptide After the Addition of Cobalt.

OBJECTIVE: To investigate whether mass spectral study would provide molecular weight information for the octapeptide and its corresponding cobalt complex.

SOLUTIONS: Ammonium acetate 20 mM, pH 7.4 (with dilute ammonia solution); $CoCl_2$ 20 μM (in HPLC grade $H_2O$); Octapeptide 9.5 μM (in HPLC grade $H_2O$).

METHOD: 20 μM $CoCl_2$ (100 μl) was added to 9.5 μM octapeptide (100 μl), and mass spectrometry was carried out.

RESULTS: The main molecular ion peak was observed at 855.4 Da, with minor peaks at 877.4 Da and 893.4 Da probably as a result of sodium and potassium cluster ions. After the addition of cobalt, an extra molecular ion peak was observed at 912.3 Da.

CONCLUSIONS: The octapeptide showed a molecular ion peak at 855 Da, consistent with the expected molecular weight of the peptide moiety. The octapeptide plus cobalt complex showed a molecular ion peak at 912 Da, suggesting that at least two protons are removed during the complex formation.

EXAMPLE 3

Spectrophotometric Analysis of the Octapeptide and Octapeptide-Cobalt Complex

OBJECTIVE: It is clear from the previous mass spectrometry evidence that cobalt forms a complex with the octapeptide with a concomitant loss of two possible protons. Metal complexes in general show distinct absorption in the UV range and in many cases these complexes show either a hypsochromic or a bathochromic shift in the spectra. These shifts can be correlated to provide the energy of binding. It was therefore anticipated that the octapeptide-cobalt complexation would provide such information.

METHOD: The quartz cuvette contained 800 μl octapeptide+200 μl $H_2O$ (control) or $CoCl_2$ (complex). Spectra were run from 180 to 800 nm on a single beam spectrophotometer.

CONCLUSIONS: Cobalt and octapeptide individually have peak absorbances at <200 and 225 nm respectively with little overlap. Following addition of a $CoCl_2$ solution to octapeptide (1.1:1) there was no significant shift in the k max (220 nm). The absorption band at this region broadened indicating complex formation, but the result could not be used to determine the binding energy (constant).

EXAMPLE 4

Mass Spectrometry of Octapeptide After the Addition of Cobalt

OBJECTIVE: To investigate whether mass spectral study would provide molecular weight information for the peptide and its corresponding cobalt complex.

METHOD: 20 or 200 µM $CoCl_2$ (100µ) was added to 22.9 µM octapeptide (100 µl) to give ratios of cobalt: octapeptide of 1:1.1 and 8.7:1 respectively. Mass spectra for the two samples were obtained as per conditions detailed in the previous example.

RESULTS: One major molecular ion peak was observed at 855.4 Da representing the octapeptide alone. After the addition of 20 EM cobalt to the octapeptide, two peaks were observed, a major peak at 855.3 representing octapeptide only plus a minor peak at 912.2 Da representing octapeptide-cobalt complex. Peak ratio of free octapeptide to octapeptide-cobalt complex was 1:0.15. A similar profile was observed following the addition of 200 µM cobalt to the octapeptide. Peak ratio of free octapeptide to octapeptide cobalt complex was 1:0.9.

CONCLUSIONS: On addition of cobalt (59 Da) to the octapeptide, the molecular ion peak should occur at 914 Da. The actual peak occurred at 912 Da, representing the loss of two protons. On addition of increasing concentrations of cobalt, the peak ratio of free octapeptide to octapeptide-cobalt complex increased.

EXAMPLE 5

The Effect of Oxygen on the Binding Capacity of the Octapeptide for Cobalt

OBJECTIVE: Previous experiments have highlighted the requirement of oxygen in promoting cobalt binding to HSA. It may be anticipated that similar effects could be observed in the manner of cobalt binding to the octapeptide.

METHOD: Octapeptide-cobalt complex (no oxygen): HPLC grade $H_2O$ was bubbled with 100% helium for 10 minutes prior to use and used to prepare the above solutions. These were further deoxygenated for 10 minutes before adding 200 µM $CoCl_2$ (2 ml) to 22.9 µM octapeptide (2 ml). This mixture was again deoxygenated for 10 minutes prior to analysis by HPLC.

Octapeptide-cobalt complex (with oxygen): HPLC grade $H_2O$ was bubbled with 100% oxygen for 10 minutes prior to use and used to prepare the above solutions. These were further oxygenated for 10 minutes before adding 200 µM $CoCl_2$, (2 ml) to 22.9 µM octapeptide (2 ml). This mixture was again oxygenated for 10 minutes prior to analysis by HPLC.

HPLC Analysis: Chromatography was carried out on a KS437 styrene/DVB polymer column (4.6 mm×150 mm, pore diameter 100–150 A, BioDynamics) under isocratic conditions of 2% acetonitrile in 30 mM Ammonium acetate pH 8.0 at a flow rate of 2 ml u min. Peaks were detected at 230 nm. Chromatography gave two distinct peaks at 230 nm, the first peak representing octapeptide-cobalt complex and the second peak representing free octapeptide. Octapeptide-$Co^{2+}$ complex formed in the presence of oxygen gave a higher ratio of complex over free peptide, as indicated by the first peak being the larger of the two. Octapeptide-$Co^{2+}$ complex formed in the absence of oxygen again gives two peaks but the second peak is now the larger of the two, indicating less complex formation.

CONCLUSIONS: It would appear that oxygenated conditions enhance cobalt binding to the octapeptide.

EXAMPLE 6

The Effect of pH on the Octapeptide

OBJECTIVE: To optimize chromatography conditions for analysis of octapeptide by HPLC.

METHOD: The octapeptide was analyzed by HPLC using a KS437 styrene/DVB Polymer column (4.6 mm×150 mm, pore diameter 100–150 A, BioDynamics) under isocratic conditions of 2% acetonitrile in 30 mM ammonium acetate at pH 6.2, 7.5 and 8.0 at a flow rate of 2 ml/min. Peaks were detected at 230 nm.

RESULTS: At pH 6.2, the octapeptide eluted after 1.6 min. At pH 8.0 the retention time had increased to 2.1 min. When the octapeptide was run at pH 7.5, two peaks were observed at 1.6 and 2.1 min.

CONCLUSIONS: The octapeptide exists in two forms depending on pH. The protonated form elutes at pH 6.2, and the deprotonated form at pH 8.0.

EXAMPLE 7

The Effect of pH on the Binding of Cobalt to the Octapeptide

OBJECTIVE: It was reported that the peptide peak 'shifted' when a solution of cobalt chloride was added to the octapeptide. It was decided to investigate this phenomenon fully as this would provide a direct tool for the determination of several parameters of cobalt binding to the octapeptide.

METHOD: 200 mM $CoCl_2$ (30 µl) was added to 2.3 mM octapeptide (270 µl), incubated at room temperature for 10 minutes and analyzed by HPLC. HPLC analysis: The octapeptide-cobalt complex was analyzed by HPLC using a KS437 styrene/DVB polymer column (4.6 mm×150 mm, pore diameter 100–150 Å, BioDynamics) under isocratic conditions of 2% acetonitrile in 30 mM ammonium acetate at pH 6.2 and 8.0 at a flow rate of 2 ml/min. Peaks were detected at 230 nm.

RESULTS: At pH 6.2, a single peak eluted after 1.6 min in the presence and absence of cobalt. At pH 8.0 however a single peak eluted after 1.2 min in the presence of cobalt and at 2.1 min in the absence of cobalt.

CONCLUSIONS: The octapeptide exists in two forms depending on pH. The protonated form that elutes at pH 6.2 is unable to bind cobalt and therefore its elution profile is unchanged. In contrast, the deprotonated form which exists at pH 8.0 is able to bind cobalt, resulting in an increased UV absorption and a decreased retention time, 1.2 min as opposed to 2.1 min for the free octapeptide.

EXAMPLE 8

The Titration of the Octapeptide with Increasing Concentrations of Cobalt

OBJECTIVE: To determine whether increasing concentrations of cobalt resulted in a corresponding increase in octapeptide-cobalt complex formation.

METHOD: Octapeptide was used at a final concentration of 2.1 mM throughout, with increasing concentrations of $CoCl_2$, as shown in the Table below:

| [$CoCl_2$] (mM) | Vol $CoCl_2$ added (µl) | [Octapeptide] (mM) | Vol octapeptide added (µl) | Ratio of octapeptide: $CoCl_2$ |
|---|---|---|---|---|
| 0 | 0 | 2.3 | 27 | 1:0 |
| 1 | 3 | 2.3 | 27 | 21:1 |
| 1.25 | 3 | 2.3 | 27 | 16.8:1 |
| 2.25 | 3 | 2.3 | 27 | 9.3:1 |
| 4.5 | 3 | 2.3 | 27 | 4.7:1 |
| 10 | 3 | 2.3 | 27 | 2.1:1 |

-continued

| [CoCl$_2$] (mM) | Vol CoCl$_2$ added (µl) | [Octapeptide] (mM) | Vol octapeptide added (µl) | Ratio of octapeptide: CoCl$_2$ |
|---|---|---|---|---|
| 18 | 3 | 2.3 | 27 | 1.2:1 |
| 36 | 3 | 2.3 | 27 | 1:1.7 |
| 72 | 3 | 2.3 | 27 | 1:3.4 |
| 200 | 3 | 2.3 | 27 | 1:9.5 |

HPLC analysis: The octapeptide-cobalt complex was analyzed by HPLC using a KS437 styrene/DVB polymer column (4.6 mm×150 mm, pore diameter 100–150 Å, BioDynamics) under isocratic conditions of 2% acetonitrile in 30 nm Ammonium acetate at pH 8.0 at a flow rate of 2 ml/min. Peaks were detected at 230 nm.

RESULTS: Mean % Peak Height:

| Final [CoCl$_2$] (mM) | Peak 1 (Octapeptide-Co complex) | Peak 2 (unknown) | Peak 3 (Octapeptide) |
|---|---|---|---|
| 0 | — | 3.72 | 96.28 |
| 0.1 | 7.44 | 7.08 | 85.49 |
| 0.125 | 9.79 | 7.55 | 82.66 |
| 0.225 | 15.65 | 15.66 | 68.52 |
| 0.45 | 25.36 | 19.67 | 54.98 |
| 1.0 | 58.66 | — | 50.42 |
| 1.8 | 61.19 | 14.97 | 23.85 |
| 3.6 | 69.55 | 13.69 | 16.76 |
| 7.2 | 71.49 | 14.47 | 14.05 |
| 20.0 | 82.17 | 10.27 | 7.56 |

From the table immediately proceeding, a plot of Log cobalt concentration versus % peak height for peak 3 was produced using Prism software. The 50% binding constant as deduced from the exponential graph had a value of 0.6461 mM.

CONCLUSIONS: For 50% binding, 0.6461 mM Co$^{2+}$ binds to 2.1 mM octapeptide. Therefore for 100% binding, 1.2922 mM Co$^{2+}$ binds to 2.1 mM octapeptide. The stoichiometry of cobalt binding to octapeptide is 0.615 cobalt to 1 octapeptide.

EXAMPLE 9

Liquid Chromatography-Mass Spectrometry of Octapeptide After the Addition of Cobalt OBJECTIVE: To investigate whether mass spectral study would provide molecular weight information for the peptide and its corresponding cobalt complex.

METHOD: 200 mM CoCl$_2$ or H$_2$O (3 µl) was added to 2.3 mM octapeptide (27 µl) and incubated at room temperature for 10 minutes. LC-MS analysis: Liquid chromatography was performed using a KS437 styrene/DVB polymer column (4.6 mm×150 mm, pore diameter 100–150 Å, BioDynamics) under isocratic conditions of 2% acetonitrile in 30 mM ammonium acetate at pH 8.0 at a flow rate of 0.5 ml/min. Peaks were detected at 230 µm, and analyzed by on-line mass spectrometry.

RESULTS: In the control sample, two molecular ion peaks were observed at 855.2 Da, representing the octapeptide alone, and at 877.2 Da, representing an octapeptide-sodium cluster. After the addition of 200 mM cobalt, one major peak was observed at 911.1 Da.

CONCLUSIONS: On addition of cobalt (59 Da) to the octapeptide, the molecular ion peak should occur at 914 Da. The actual peak occurs at 911 Da, representing the loss of protons

EXAMPLE 10

Endoprotease Lys-C Digest of the Octapeptide and its Subsequent Incubation with Cobalt OBJECTIVE: Previous experiments confirm that CoCl$_2$ forms a stable complex with the octapeptide. In order to elucidate the site of attachment, the octapeptide was cleaved stereoselectively with the endoprotease Lys-C. The resultant tetrapeptides upon incubation with CoCl$_2$ would allow elucidation of the probable binding site.

METHOD: Octapeptide 1.97 mg/ml (250 µl) was incubated with the endoprotease Lys-C 100 µg/ml (50 µl) at a substrate: enzyme ratio of 100:1 (w/w) in 8.3 mM Tricine, 1.6 mM EDTA pH 8.0 at 37° C. for 24 h. After digestion, 27 µl of the product was incubated with 200 mM CoCl$_2$ (3 µl) at 20° C. for 10 minutes prior to analysis by HPLC. HPLC Analysis: The products from the Lys-C digest were analyzed by HPLC using an amino column (4.6 mm×250 mm, pore diameter 100 Å, BioDynamics-73) under isocratic conditions of 30 mM ammonium acetate at pH 8.0 at a flow rate of 1.5 ml/min. Peaks were detected at 230 nm.

RESULTS: When the digested Lys-C products were run on HPLC, two peaks were observed at 2.6 and 8.9 min, designated tetrapeptides 1 and 2 respectively. Similarly after addition of cobalt to the digested products two peaks were again observed. However, tetrapeptide 1 exhibited an increased UV absorption and decreased retention time, eluting at 1.7 min. as opposed to 2.6 min.

CONCLUSIONS: The octapeptide was digested at the C terminus of the lysine residue by the endoprotease yielding two tetrapeptides. On addition of cobalt to the endoprotease digested octapeptide, a single tetrapeptide-cobalt complex was formed with tetrapeptide 1. There appeared to be no effect on tetrapeptide 2.

EXAMPLE 11

Mass Spectrometry Analysis of the Tetrapeptide 1—Cobalt Complex

OBJECTIVE: To determine the identity of tetrapeptide 1.

EXPERIMENTAL: Tetrapeptides 1 and 2 were fractionated by HPLC and collected (experiment 59). CoCl$_2$ 1.2 mM (3 µl) was added to tetrapeptide 1 (27 µl) and incubated at room temperature for 10 minutes. Samples were subsequently run on MS as described previously.

RESULTS: Tetrapeptide 1 gave two molecular ion peaks at 470.1 and 477.1 Da. Tetrapeptide 2 gave a single peak at 404.0 Da. Tetrapeptide 1-cobalt complex gave two peaks at 477.1 and 526 Da.

CONCLUSIONS: Tetrapeptide 1 is determined to be Asp-Ala-His-Lys [SEQ ID NO:1] with a molecular weight of 469 Da. Tetrapeptide 2 is determined to be Ser-Glu-Val-Ala [SEQ ID NO:3] (404 Da). Cobalt binds to Asp-Ala-His-Lys [SEQ ID NO:1] forming a complex of 526 Da with a loss of 3 protons. The molecular ion peak observed at 477.1 Da is a contaminant from the Lys-C preparation.

EXAMPLE 12

Free radicals were generated by incubating the octapeptide with a photosensitizing agent, such as photofrin® (porfimer sodium) followed by activation by illumination with an appropriate wavelength of light. Exposure to light, especially in the red range (630 nm), in the presence of oxygen resulted in the formation of superoxide and hydroxyl free radicals. These free radicals in turn reacted with amino acids in the N-terminus of albumin. It was found that, after such treatment, the octapeptide binding of cobalt is significantly reduced (to almost 100%—time and radiation dose dependent). NMR analysis revealed a change in the alanine in position 2 potentially due to the loss of a proton on the backbone of alanine causing cyclization of the aspartate carboxyl group with the alanine carbon.

Specific Experimental Procedure:

All steps were carried out in a Tris buffer 300 mM, pH 7.5. Two ml of octapeptide at 1 mg/ml were incubated with 40 µl photofrin® (porfimer sodium) solution, 70 mg/ml. The solution had a brownish color and was exposed to intense fluorescent light that included 630 mm for periods of 30 to 120 minutes. The solution was then subjected to HPLC with and without the addition of Co and the chromatograms were compared. The HPLC method consisted of an isocratic run using 2% acetonitrile and 98% ammonium acetate, 30 mM, pH 8.0, at 1 ml/minute using a Ultrahydrogel 120 column at 60 degrees Celsius and detection at 214 nm. Using this method showed that the octapeptide was clearly subjected to the photofrin® and radiation did not bind cobalt. Appropriate controls were conducted.

In Vivo Models

EXAMPLE 13

Sample Handling Procedures

The sample which may be used in the present invention may be obtained from any tissue or fluid sample taken from a patient, or from commercial vendor sources. Appropriate fluid samples include whole blood, venous blood, blood serum, plasma, as well as other body fluids such as amniotic fluid, lymph, cerebrospinal fluid, saliva, etc. The sample may be obtained by well known conventional biopsy and fluid sampling techniques. Preferred samples are blood plasma, serum and purified albumin. Purified albumin may be isolated from the serum by any known technique, which would include electrophoresis, ion exchange, affinity chromatography, gel filtration, etc.

Blood samples are taken using Universal Precautions. Peripheral venipuncture is performed with the tourniquet on less than 30 seconds (contralateral arm from any IV fluids). Blood is drawn directly into two 10 cc Becton Dickinson Vacutainer® Sodium-Heparinized tubes. Gently invert once to mix. If an IV port is used, the blood can be collected (after a discard sample is drawn equivalent to the dead space of usually 5 cc) into a plain syringe and dripped gently down the side of two 10 cc Becton Dickinson Vacutainer® brand tubes. Gently invert once to mix. Blood may also be collected directly from the Vacutainer® tubes with special administration sets with a reservoir system that do not require a discard sample. These systems allow a draw to be taken proximal to the reservoir.

Plasma tubes must be centrifuged within 2 hours of the draw. (Note, if serum is collected, it must clot between 30–120 minutes at room temperature (RT) before centrifugation. Ring the inside of the serum tube with a wooden applicator to release the clot from the glass before centrifugation. If the subject is taking anticoagulants or has a blood clotting dysfunction, clot longer than 60 minutes, between 90–120 minutes best.) Centrifuge tubes for 10 minutes at RT at 1100 g (<1300 g). Pool collected samples in a plastic conical t in tube and invert once to mix.

If the sample will not be used within 4 hours of centrifugation, the sample should be frozen. Alternatively, separated serum may be refrigerated at 4° C. until tested, but should be tested within 8 hours (storage over 24 hours may result in degradation of the sample).

EXAMPLE 14

Test Method for Detecting Occurrence or Non-Occurrence of Marker Using Cobalt Binding The occurrence or non-occurrence of the marker was detected as follows: 200 µl of patient sera are added to each of two tubes each containing 50 µl 0.11% $COCl_2$ $6H_2O$. The mixture is allowed to react at room temperature (18–25° C.), or higher, for 5 or more minutes. Thereafter, 50 µl 0.01 M dithiothreitol (DTT) is added to one of the two tubes (the "test tube") and 50 µl 0.9% NaCl is added to the second tube (the "background tube"). After two minutes, 1 ml 0.9% NaCl is added to both tubes. Absorbance spectroscopy at 470 nm measurements are taken of the two tubes. The marker was considered present if the optical density was greater than or equal to 0.400 OD (or alternatively a clinically derived cut-off) using a spectrophotometer at OD at 470 nm.

Equivalent materials which may be used as alternatives include any of the transition metals. Ferrozine or other compounds with an affinity to cobalt can be substituted for DTT and/or any cobalt or metal coloring reagent. $CoCl_2.6H_2O$, for instance, can be utilized. The optimal range for cobalt binding to albumin is from pH 7 to pH 9, with a range of pH 7.4–8.9 being most preferred; pH 9 is optimal for cobalt interaction with the color reagent. The amount of serum sample can also vary, as can the amounts of $CoCl_2.6H_2O$ and DTT and ferrozine. Critical, however, is that the amount of cobalt used be in excess of the amount of albumin and that the DTT or ferrozine be in excess of the cobalt.

EXAMPLE 15

Test Method for Detecting Occurrence or Non-Occurrence of Marker Using Measurement of Copper Albumin was purified from 0.2 cc of human serum or plasma using an ion exchange method to produce approximately 8 mg of purified albumin. A buffer having a pH in the range of 7 to 9 is added. The amount of copper present in the sample is then measured by direct spectrophotometric and potentiometric methods, or by any of several other known methods, including atomic absorption, infrared spectroscopy, HPLC and other standard or non-standard methods, including radioactive tracer techniques. The proportion of copper to albumin is used as a measure of the quantity of the marker present, the greater the proportion, the higher the quantity of marker present.

EXAMPLE 16

Method of Using Marker to Assess Clinical Efficacy of Photosensitzing Agents Used in Photodynamic Therapy for the Treatment of Tumors A method of the present invention uses the marker to assess the clinical efficacy of photosensitizing agents (and light-activated compounds) used in photodynamic therapy for the treatment of tumors, such as Photofrin® (porfimer sodium).

Prior to administration with the photosensitizing chemotherapeutic agent, a biological sample containing albumin is obtained from the patient and a baseline value of the marker present is obtained. Detection and measurement of the marker may be by any of the methods included herein, including those of Examples 14 and 15.

Standard procedure for treatment with photosensitizing chemotherapeutic agent is followed. For instance, in the palliative treatment of dysphagia due to completely obstructing esophageal carcinoma, one dose of Photofrin® (porfimer sodium) is injected intravenously at 2 mg/Kg over 3–5 minutes. Low energy, non-thermal laser light (630 nm wavelength) is applied forty to fifty hours after injection, directly to the vicinity of the tumor. Sucessful laser-induced photochemical activation of the Photofrin® will result in cellular damage of tumor cells and accordingly, the propagation of free radicals. Detection of the existence of the marker, and a corresponding change in the level thereof during the application of the laser, will provide an indication (and measurement) of the effectiveness of the photodynamic therapy.

Tumor selectivity in treatment occurs through selective retention of Photofrin® and selective delivery of light. Thus, various tumor sites may be treated. However, in other applications, laser light application may require invasive, including surgical, procedures and accordingly, may occur prior to, simultaneously with or subsequent to surgical removal of the tumor. At several time intervals during light application, albumin-containing biological samples may be obtained and tested for the occurrence or non-occurrence of the marker. The level of the marker detected may be measured specifically. Detection of the existence of the marker, and a rise thereof, during the application of the laser indicates effectiveness of the photodynamic therapy.

EXAMPLE 17

In patients undergoing photodynamic therapy for glioblastoma multiforme cancer, blood samples were collected before and after photolysis. Detection and measurement of the marker occurred in accordance with the method of Example 14. The test result after photodynamic therapy showed an increase of free radical damage of albumin that resulted in approximately 50% reduction of cobalt binding to albumin.

Results:

|  | Before photodynamic therapy | After photodynamic therapy |  |
|---|---|---|---|
| Patient 1 | 0.251 | 0.356 | 41.8% increase |
| Patient 2 | 0.148 | 0.234 | 58.1% increase |

The above description of the invention, including Examples 1 through 17, is intended to be illustrative and not limiting. Various changes or modification in the embodiments described may occur to those skilled in the art. These can be made without departing from the spirit or scope of the invention.

We claim:

1. A method of monitoring or assessing treatment of a disease or condition with a compound that produces or reduces free radicals comprising:

obtaining a first biological sample from a patient suffering from the disease or condition, the biological sample containing albumin and possibly containing a modified albumin having a reduced ability to bind metal ions at its N-terminus;

treating the patient with the compound;

obtaining one or more additional biological samples of the same type from the same patient at one or more times after the treatment; and determining if there is a change in the quantity of the modified albumin present in the first sample as compared to the subsequent sample(s), the quantity of the modified albumin in each sample being indicative of the amount of free radical damage in that sample, and a change in the quantity of the modified albumin in the first sample as compared to the subsequent sample(s) being indicative of a change in the amount of free radical damage and, therefore, of the effectiveness or ineffectiveness of the treatment, the determination being made by:

(a) contacting each of the biological samples with an excess quantity of a metal ion salt, the metal ion being capable of binding to the N-terminus of unmodified human albumin, to form a mixture of bound metal ions and unbound metal ions;

(b) determining the amount of bound metal ions for each biological sample, the amount of bound metal ions providing a measure of the quantity of the modified albumin in the sample; and (c) determining if there is a change in the amount of bound metal ions between the first and subsequent sample(s), the change in the amount of bound metal ions providing a measure of the change in the quantity of the modified albumin between the first and subsequent sample(s).

2. The method of claim 1 wherein the compound is a free radical scavenger.

3. The method of claim 2 wherein the free radical scavenger is selected from the group t, consisting of superoxide dismutase, catalase, glutathione peroxidase, ebselen, glutathione, cysteine, N-acetyl cysteine, penicillamine, allopurinol, oxypurinol, ascorbic acid, α-tocopherol, water-soluble α-tocopherol, β-carotene, fatty-acid binding protein, fenozan, probucol, cyanidanol-3, dimercaptopropanol, indapamide, emoxipine, and dimethyl sulfoxide.

4. The method of claim 1 wherein the compound is a photosensitizing agent used in photodynamic therapy for the treatment of tumors.

5. The method of claim 4 wherein the compound is porfimer sodium.

6. The method of claim 1 wherein said sample is serum or plasma.

7. The method of claim 1 wherein said metal ion salt is a salt of a metal selected from the group consisting of V, As, Co, Sb, Cr, Mo, Mn, Ba, Zn, Ni, Hg, Cd, Fe, Pb, Au and Ag.

8. The method of claim 1 wherein said metal ion salt is a salt of cobalt.

9. The method of claim 1 wherein step (b) is conducted using atomic absorption or atomic emission spectroscopy.

10. The method of claim 1 wherein said excess quantity of metal ion salt is a predetermined quantity, and the quantity of unbound metal ions is detected to determine the amount of bound metal ions.

11. The method of claim 10 wherein detection of the quantity of unbound metal ions is conducted using atomic absorption or atomic emission spectroscopy.

12. The method of claim 10 further comprising the steps of:

adding a compound having the formula Asp-Ala-His-Lys-R, wherein R is a group capable of being detected when the compound is bound to the metal ion of said metal ion salt, to the mixture containing bound metal ions and unbound metal ions; and detecting the quantity of R to detect the quantity of unbound metal ions.

13. The method of claim 12 wherein the determination of the quantity of said compound which is complexed with said metal ion is conducted using atomic absorption or atomic emission spectroscopy.

14. The method of claim 10 wherein:

the metal ion salt is a salt of a metal selected from the group consisting of V, As, Co, Sb, Cr, Mo, Mn, Ba, Zn, Ni, Hg, Cd, Fe, Pb, Au and Ag;

the mixture of bound metal ions and unbound metal ions is contacted with an aqueous color forming compound solution to form a colored solution, said compound being able to form color when bound to the metal ions; and the color intensity of said colored solution is determined to determine the quantity of unbound metal ions to provide a measure of bound metal ions.

15. The method of claim 14 wherein said color forming compound is ferrozine.

16. The method of claim 14 wherein said metal ion salt is a salt of cobalt.

* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Homo sapiens

<400> SEQUENCE: 1

Asp Ala His Lys
1

<210> SEQ ID NO 2
<211> LENGTH: 8
<212> TYPE: PRT
<213> ORGANISM: Homo sapiens

<400> SEQUENCE: 2

Asp Ala His Lys Ser Glu Val Ala
1               5

<210> SEQ ID NO 3
<211> LENGTH: 4
<212> TYPE: PRT
<213> ORGANISM: Homo sapiens

<400> SEQUENCE: 3

Ser Glu Val Ala
1
```